United States Patent [19]

Neumeyer et al.

[11] Patent Number: 4,687,773

[45] Date of Patent: Aug. 18, 1987

[54] (+)-N-N-PROPYLNORAPOMORPHINE AND SELECTIVE LIMBIC ACTIVITY

[75] Inventors: John L. Neumeyer, Wayland; Ross J. Baldessarini, Newton, both of Mass.

[73] Assignees: McLean Hospital, Belmont; Northeastern University, Boston, both of Mass.

[21] Appl. No.: 739,612

[22] Filed: May 31, 1985

Related U.S. Application Data

[63] Continuation-in-part of Ser. No. 479,219, Mar. 28, 1983, abandoned.

[51] Int. Cl.$^4$ .................. A61K 31/47; C07D 221/18; C07D 491/06
[52] U.S. Cl. ................................ 514/280; 514/284; 546/48; 546/75
[58] Field of Search ................. 546/48, 75; 514/280, 514/284

[56]  References Cited

U.S. PATENT DOCUMENTS

| | | | |
|---|---|---|---|
| 3,717,639 | 2/1973 | Neumeyer | 546/75 |
| 3,717,643 | 2/1973 | Archer | 546/75 |
| 3,810,987 | 5/1976 | Saari | 546/75 |
| 4,353,912 | 10/1982 | Neumeyer | 424/258 |
| 4,543,256 | 9/1985 | Neumeyer | 514/280 |

OTHER PUBLICATIONS

Ram et al., J. Org. Chem., vol. 46, pp. 2830-2831 (1981).
Campbell et al., Neuropharmacology, vol. 24, pp. 391-399 (1985).
Lal et al., Chemical Abstracts, vol. 78, 92509j (1973).
Sheppard et al., Chemical Abstracts, vol. 90, 116902j (1979).
Saari et al., J. Med. Chem., vol. 17, No. 10, pp. 1086-1090 (1974).
Neumeyer et al., J. Med. Chem., vol. 17, No. 10, pp. 1090-1095 (1974).
Baldessarini et al., Biochemical Pharmacology, vol. 26, pp. 1749-1756 (1977).
Davis et al., J. Pharm. Sci., vol. 69, No. 9, pp. 1056-1058 (1980).
Neumeyer et al., J. Med. Chem., vol. 24, No. 12, pp. 1440-1445 (1981).
Neumeyer et al., Abstracts of Papers, North American Medicinal Chemistry Symposium, University of Toronto, Toronto, Canada, p. 48, 6/82.
Neumeyer et al., J. Med. Chem., vol. 26, No. 4, pp. 516-521 (04/83).
Riffee et al., Chemical Abstracts, vol. 97, 85170f (1982).
Heikkila et al, Chemical Abstracts, vol. 98, 192339k (1983).
Baldessarini et al., Eur. J. Pharmacol., vol. 77, No. 1, pp. 87-88 (1982).
Hinsie et al., "Psychiatric Dictionary", Oxford University Press, New York (1970), pp. 619-620.
Costall et al., European J. Pharmacology, vol. 35, pp. 161-168 (1976).
American Psychiatric Association, "A Psychiatric Glossary" (1980), pp. 64, 123.
Coyle et al., ed., "Neuroleptics: Neurochemical, Behavioral, and Clinical Prospectives", Raven Press, New York (1983), pp. 1-2, 12, 93-117, 119, 150.
Karasu, ed., "The Psychiatric Therapies", American Psychiatric Association, Washington, D.C. (1984), pp. 119-120.
Goodman & Gilman's "The Pharmacological Basis of Therapeutics", 7th ed., Macmillan Pub. Co., New York (1985), pp. 339, 340, 387, 391.
Baldessarini, "Chemotherapy in Psychiatry", Harvard U. Press, Cambridge, Mass. (1985), pp. 14-15, 37-46, 235-236.
Campbell et al., Psychopharmacology, vol. 88, pp. 158-164 (1986).
Campbell et al., Brain Research, in press.

Primary Examiner—Donald G. Daus
Assistant Examiner—Diana G. Rivers
Attorney, Agent, or Firm—Weingarten, Schurgin, Gagnebin & Hayes

[57]  ABSTRACT

Antidopaminergic agents having selective limbic activity, comprising (S)-enantiomers of aporphine compounds of either the following structures:

(Abstract continued on next page.)

or wherein $R_1$ is lower alkyl, alkyl substituted lower alkyl, alkyl substituted cycloalkyl, lower alkenyl, alkyl substituted lower alkenyl, lower alkynyl, alkyl substituted lower alkynyl, phenyl lower alkyl, phenyl lower alkenyl, and phenyl lower alkynyl, and the following structure where $R_1$ is as above and $R_2$ and $R_3$ are hydrogen, methyl, or $R_1$

12 Claims, 2 Drawing Figures

FIG. 1

FIG. 2

(+)-N-N-PROPYLNORAPOMORPHINE AND SELECTIVE LIMBIC ACTIVITY

This application is a continuation-in-part of a copending application, Ser. No. 479,219 filed Mar. 28, 1983 now abandoned which is included herein by reference.

FIELD OF THE INVENTION

The invention relates to novel aporphine compounds. In particular, it relates to certain S-enantiomers of aporphines which have selective limbic activity.

BACKGROUND OF THE INVENTION

Compounds previously described as having use as antipsychotic agents block both the limbic and striatal dopamine systems, resulting in undesirable side effects and toxicity as well as clinically useful actions.

SUMMARY OF THE INVENTION

An important neuropharmacologic difference has been found between the enantiomers of aporphines represented by the S(+) and R(−) enantiomers of apomorphine (APO) and N-propylnorapomorphine (NPA).

Unlike R(−) aporphines, the S(+) isomers of APO and NPA are virtually without ability to induce general behavioral arousal or stereotyped gnawing reactions in the rat, behaviors which represent stimulation of dopamine (DA) receptors in the limbic system and basal ganglia (corpus striatum), an extra-pyramidal motor center, respectively. Data to indicate the contrasting actions of the (+) and (−) enantiomers of APO and of NPA are shown hereinafter.

Data hereinafter provided support the conclusion that the S(+) aporphines act as DA receptor antagonists in the limbic system but not in the basal ganglia in pharmacologically appropriate doses.

(+)NPA was found not only to lack the general motor activating action of (−)NPA, but to produce dose-dependent inhibition of such activity of the R(−) aporphine. This discovery led to the conclusion that (+) isomers of APO or NPA have selective anti-DA actions in forebrain centers selective for the locomotor and arousal effects of DA, mainly in the limbic system, such as has been demonstrated by direct injections of DA into the nucleus accumbens septi, a region rich in limbic DA projections and DA receptors.

Tables presented hereinafter indicate that the (+) enantiomers of APO and NPA fail to interfere with the stereotyped actions of their respective (−) isomers, given at a range of doses. They reduce locomotor-arousal activity induced by the (−) isomers, as detected by an electronic activity monitor, and (+)NPA also reduces spontaneous locomotor activity without inducing extrapyramidal actions such as catalepsy. The interaction of (+) isomers with low doses of the corresponding (−) enantiomer, has a marked dose-dependent inhibitory action on the locomotor actions of (−) aporphines. The half-maximally effective dose ($ID_{50}$) of s.c. (subcutaneous) (+)APO to reduce the locomotor activating actions of (−)APO (0.3 mg/kg, s.c.) was 4 mg/kg; similarly, the value for (+)NPA of 0.2 mg/kg indicated an even more striking and potent effect of (+)NPA (20×more potent) as a selective locomotor inhibitor capable of counteracting the effects of a DA agonist. Moreover, (+)NPA inhibited spontaneous locomotor arousal at an $ID_{50}$ of 3 mg/kg ($ID_{50}$ for (+)APO>50 mg/kg). In addition, S(+) 11-hydroxy-N-propylnoraporphine exerted similarly selective actions as (+)NPA, while S(+) 11-hydroxyaporphine (N−R=N-methyl) was less active. Moreover, S(+)NPA blocked the behavioral-arousal induced by DA placed stereotaxically in the rat nucleus accumbens ($ID_{50}$=0.4 mg/kg, i.p.) while (+)APO had only a weak effect ($ID_{50}$=4 mg/kg); neither (+) aporphine blocked the postural changes induced by local injection of DA into the corpus striatum. The methylendioxy derivative of S(+)NPA was also active after systemic oral administration, selectively, against DA placed in the accumbens but not the striatum.

In summary, the (+) enantiomers of (+)NPA and its analogs as discussed are selective anti-DA agents for arousal mechanisms associated with the limbic system. Since traditional antipsychotic agents have nonselective anti-DA effects in extrapyramidal as well as limbic DA receptors, they are almost all associated with extrapyramidal neurological side effects as the price for their clinically useful antipsychotic effects.

As used herein, the term "lower-alkyl" means saturated monovalent aliphatic radicals, including straight and branched-chain radicals, of from two to six carbon atoms, as illustrated by, but not limited to, ethyl, propyl, isopropyl, butyl, sec.-butyl, amyl, or hexyl.

As used herein, the term "lower-alkenyl" means monovalent, aliphatic radicals of from three to seven carbon atoms which contain at least one double bond, and are either straight or branched-chain, as illustrated by but not limited to 1-(2-propenyl), 1-(3-methyl-2-propenyl), 1-(1,3-dimethyl-2-propenyl), or 1-(2-hexenyl).

As used herein, the term "lower-alkynyl" means monovalent, aliphatic radicals of from three to seven carbon atoms which contain at least one triple bond, and are either straight or branched, as illustrated by, but not limited to, 1-(2-propynyl), 1-(1-methyl-2-propynyl), or 1-(2-heptynyl).

As used herein, the term "cycloalkyl" means cyclic, saturated aliphatic radicals of from three to eight ring carbon atoms, as illustrated by but not limited to cyclopropyl, cyclobutyl, 2-methylcyclobutyl, cyclohexyl, 4-methylcyclohexyl, or cyclooctyl.

As used herein, the terms "phenyl-lower-alkyl," "phenyl-lower-alkenyl," and "phenyl-lower-alkynyl" mean monovalent radicals consisting of a phenyl nucleus bonded to the rest of the molecule through, respectively, a divalent lower-alkylene radical of from one to four carbon atoms, as illustrated by, but not limited to, methylene, 1,1-ethylene, 1,2-ethylene, 1,3-propylene, 1,2-propylene, or 1,4-butylene; or through a divalent lower-alkynylene radical of from two to four carbon atoms, as illustrated by, but not limited to, 1,2-ethynylene, 1,3-propynylene, 1,3-(1-butynylene), and the like. Moreover, the benzene ring of such phenyl-lower-alkyl, phenyl-lower-alkenyl, and phenyl-lower-alkynyl radicals can be substituted by one or more substitutes selected from the group consisting of lower-alkyl, lower-alkoxy, halo (chloro, bromo, iodo, or fluoro), nitro, lower-alkylmercapto, methylenedioxy, and trifluoromethyl.

Appropriate acid addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexane-carboxylic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, benzenesulfinic acid, butylarsonic acid, p-toluenesulfonic acid, benzenesulfinic acid, butylarsonic acid, diethylphosphinic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

S-enantiomers of aporphines of the following structure are dopamine antagonists with selective limbic activity:

wherein $R_1$ is lower alkyl, alkyl-substituted lower alkyl, cycloalkyl, alkyl-substituted cycloalkyl, lower alkenyl, alkyl substituted lower alkenyl, lower alkynyl, alkyl-substituted lower alkynyl, phenyl lower alkyl, phenyl lower alkenyl, and phenyl lower alkynyl. Also included within the scope of this invention are such compounds wherein the 10,11 positions are bridged by a dioxy group characterized as being cleaved in vivo to provide the compound with two adjacent hydroxy groups, as, for example, wherein $R_2$ and $R_3$ are hydrogen, methyl, or $R_1$.

As one example of this invention, (+)-N-n-propylnorapomorphine (+NPA) has a marked motor-inhibitory effect with little effect on stereotyped gnawing. This is quite unexpected and surprising, since neuroleptic compounds which have been used as antipsychotic agents have similar effects in both striatial and limbic systems, usually resulting in toxic neurological side effects. By bridging the 10,11 hydroxyl groups with a methylenedioxy function or analogs, these compounds can be administered orally.

The S(+)-enantiomers are prepared from the racemic mixtures by reacting the racemic mixtures with (+)dibenzoyl-D-tartaric acid and isolating by crystallization. Racemic mixtures can be obtained from the 10,11 R-enantiomers by first converting to the 10,11-dimethyl ether with CH₂N₂, then reacting with 10% palladium on carbon in acrylonitrile, followed by reacting with NaCNBH₃ in ethanol to obtain the racemic dimethyl ether. The racemic 10,11-dihydroxy compound is obtained by splitting the ether with HBr in acetic acid. Racemic mixtures of 10,11-methylenedioxy and similar bound forms are prepared from the R-enantiomers by reacting with 10% palladium on carbon in acrylonitrile, followed by reacting with NaCNBH₃. Further details on the procedures are found in the experimental section pending publication below and references cited therein. Procedures for preparation of R-enantiomers of 10,11-methylenedioxy and similar bound forms of aporphines are described in the copending patent applications of John L. Neumeyer, Ser. No. 379,557 filed May 18, 1982, now U.S. Pat. No. 4,543,256; Ser. No. 358,918 filed Mar. 17, 1982; Ser. No. 358,917 filed Mar. 17, 1982; Ser. No. 346,841 filed Feb. 8, 1982; and Ser. No. 274,772 filed June 18, 1981, all said applications being incorporated herein by reference.

In addition, we have found that S(+) enantiomers of aporphines having the following structure also produce significant inhibition of arousal and are inactive as dopamine agonists in forebrain dopamine receptors:

wherein $R_1$ is lower alkyl, alkyl substituted lower alkyl, cycloalkyl, alkyl substituted cycloalkyl, lower alkenyl, alkyl substituted lower alkenyl, lower alkynyl, alkyl substituted lower alkynyl, phenyl lower alkyl, phenyl lower alkenyl and phenyl lower alkynyl and pharmaceutically acceptable acid addition salts thereof and $R_4$ is hydrogen, methyl, lower alkyl or $R^1CO$ where $R^1$=methyl or lower alkyl.

CHEMISTRY

Figure 1:
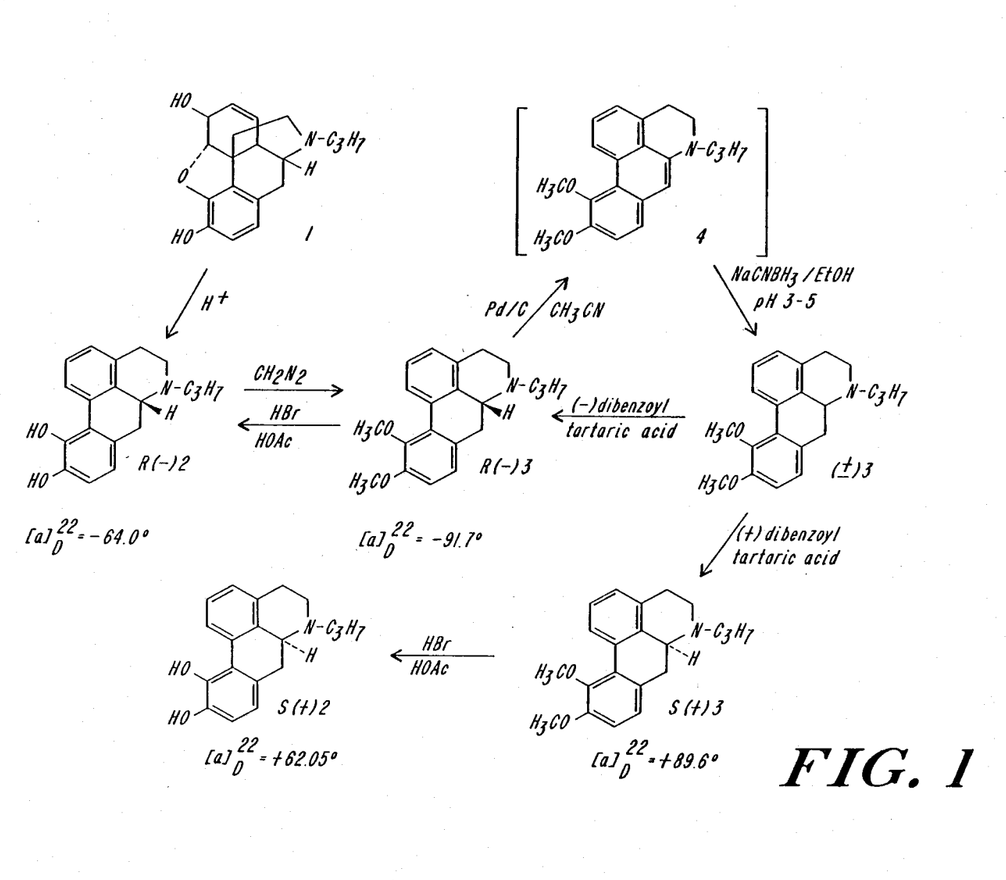

The acid-catalyzed rearrangement of morphine or N-n-propylnormorphine (1) (FIG. 1) is a well-established method for obtaining (R)-apomorphine[1] or (R)-N-n-propylnorapomorphine [(R)-(−)-2.][2] The conversion of 2 to its dimethyl ether (3) was accomplished with diazomethane by a published method.[3] The 10,11-O,O'-dimethyl ether of NPA, (±)-3, was obtained by a multistep procedure from vanillin and isoquinoline[3] (FIG. 1).

We found that (+)-dibenzoyl-D-tartaric acid was a convenient resolving agent for the resolution of (RS)-3; after three recrystallizations from a mixture of EtOAc/2-propanol, a diastereoisomeric salt with a constant specific rotation was obtained. Ether cleavage with HBr yielded (S)-2, which, by gradient HPLC, [15 cm×4.6 mm upelosil LC-18 column: exponential gradient from 30% acetonitrile/70% buffer to 80% acetonitrile/20% buffer over a 10 min period at a flow rate of 2 mL/min] indicated a product of greater than 99% chemical purity. The circular dichroism (CD) spectra of (S)-2-HCl and (R)-2-HCl are shown in FIG. 1. The most intense extrema for the Cotton effect were observed at 232 nm with molar ellipticies of −25.9 and +25.8×10 units for R and S configurations, respectively. The R/S ratio is 1.004, which suggests the relative enantiomeric purity of the two isomers of N-n- propylnorapomorphine utilized for our biological studies.

The combined mother liquors containing enriched (R)-3, obtained after resolution of (S)-3, when treated with (−)-dibenzoyl-L-tartaric acid led to the isolation of (R)-3-HCl. The racemization of (R)-3 to (RS)-3 was accomplished with 10% palladium on carbon in acetonitrile according to the method of Cava et al.[4] Reduction of the dehydroraprophine 4 with NaCNBH$_3$ in EtOH at pH 5 by modifications of the method used by Davis et al[5] for the racemization of (R)-apomorphine dimethyl ether provided an alternative method for the synthesis of the S antipode rather than the de novo synthesis also used for the preparation of (R,S)-3.

GENERAL METHODS

All melting points were determined on a Thomas-Hoover apparatus and are uncorrected. Elemental analyses were performed by Galbraith Laboratories, Knoxville, TN. Thin-layer chromatography (TLC) used recoated silica gel 13179, polyethyleneterphthalate sheets (Eastman Kodak, Rochester, NY). Ultraviolet spectra were recorded in acetonitrile on a Perkin-Elmer Lamda 5 spectrophotometer. Circular dichroism spectra were recorded in acetonitrile on a JASCO Model 500C CD spectropolarimeter. Optical rotations were obtained on a Perkin-Elmer polarimeter (Model 241).

Resolution of 10,11-Dimethoxy-N-n-propylnoraporphine [(R)- and (S)-3]. To a solution of 6.0 g (19 mmol) of (±). 10,11-dimethoxy-N-n-propylnoraporphine [(RS)-3$^3$ dissolved in 35 mL of EtOAc was added a solution of 7.0 g (190 mmol) of (+)-dibenzoyl-D-tartaric acid [Sigma Chemical Co.]; $[\alpha]_D^{22} + 124°$ (c 1.2, EtOH)] dissolved in 35 mL EtOAc containing 2 mL of 2-propanol. The mixture was heated to reflux for 10 min and then filtered and cooled. After the mixture was left standing at 0° C. for 3 days, 3 g of gray crystals was collected. This (+)-dibenzoyl-D-tartrate salt was crystallized three times from a mixture of 30 mL of EtOAc, 15 mL of 2-propanol, and 15 mL of EtOH: mp 154°-155° C.; yield 0.5 g. Further recrystallizations did not change the specific rotation: $[\alpha]_{578}^{22} + 115.0°$ (c 0.2 MeOH).

The crystalline salt was dissolved in aqueous saturated Na$_2$CO$_3$ solution, and the mixture was extracted with CHCl$_3$. After drying (Na$_2$SO$_4$), the extract was converted into the hydrochloride salt to give 336 mg of an off-white powder of (S)-3-HCL: mp 110°-115° C.; $[\alpha]_D^{22} + 89.6°$ (c 0.18, MeOH).

The combined mother liquors containing the (R)-(−)-3 salt were treated with aqueous saturated Na$_2$CO$_3$ solution to liberate the free base, extracted with EtOAc, dried, and evaporated to dryness. The remaining 5.5 g of oil was dissolved in 35 mL of EtOAc and treated with 6.6 g (18 mmol) of (−)-dibenzoyl-L-tartaric acid (Sigma Chemical Co.; $[\alpha]_D^{22} - 121.6°$ (c 0.5, EtOH)] and treated as described above to give 1.0 g of the (R)-3 salt, mp 154°-155° C.: $[\alpha]_{578}^{22} - 114.64°$ (c 0.25, MeOH). The crystalline salt was dissolved in aqueous saturated Na$_3$CO$_3$ solution and the mixture was extracted with CHCl$_3$. After drying (Na$_2$SO$_4$), the extract was converted to the hydrochloride salt to give 0.43 g of (R)-(−)-3-HCL mp 112°-116° C.; $[\alpha]_D^{22} - 91.7°$ (c 0.22, MeOH).

(RS)-N-n-Propylnorapomorphine hydrodide was prepared via a multistep synthesis by a method previously described.[3]

(S)-N-n-Propylnorapomorphine Hydrochloride [(S)-2-HCl]. To 0.3 g (0.97 mmol) of (S)-3-HCl) dissolved in 10 mL of glacial AcOH was added 10 mL of HB: (48% w/v). The reaction mixture was heated under an atmosphere of N$_2$ at reflux in an oil bath for 4 h and then allowed to cool under nitrogen. Monitoring of the mixture by TLC indicated that complete ether cleavage had occurred. To the cooled (ice bath) reaction mixture was added 100 mg of NaHSO$_3$. The pH of the solution was adjusted to 8 with aqueous Na$_2$CO$_3$ solution, and the liberated free base was extracted from CHCl$_3$ and converted to the hydrochloride salt: yield 235 mg (76%) of (S)-2-HCl: mp 178°-180° C.: $[\alpha]_D^{22} + 62.05°$ (c 0.166, MeOH); UV$\lambda_{max}$ 274 nm with a broad shoulder at 312 nm. (R)-(−)-2-HCl obtained by the rearrangement of 1, gave $[\alpha]_D^{22} - 63.21°$ (c 0.166, MeOH).

Racemization of (R)-10,11-Dimethoxy-N-n-propylnoraporphine. (R)-2 (3.5 g, 11 μmol) in 160 mL of CH$_3$CN was allowed to reflux with 3.2 g of 10% Pd on charcoal under an atmosphere of nitrogen. After 12 h, TLC indicated complete conversion to the dehydroaporphine (4). The catalyst was filtered off, and the filtrate was evaporated to give a green oil; this was dissolved in 420 mL of absolute EtOH, and 3.5 g (55 mmol) NaBH$_3$CN was added; EtOH/HCl was added until the pH was 5.0. The pH was maintained over 24 h by several additions of the EtOH/HCL. After evaporation of the reaction mixture, the pH was adjusted to 8 with saturated aqueous Na$_3$CO$_3$ solution, and the free base was extracted from CHCl$_3$ as 2.8 g of a yellow oil: $[\alpha]_D^{22}0°$ (c 0.24, MeOH). The oil was converted to [(±)-3-HCl], mp 235°-236° C. dec. The demethylation of (±)-3-HCl with HBr was carried out as described above and gave (±)-2-HCl, mp 258°-259° C. dec.

S(+) 10,11-methylenedioxy-N-propylnoraporphine hydrochloride [(+)]-MDO-NPA

A solution of R(−)10,11-methylenedioxy-N-n-propylnoraporphine[6] [(−)MDO-NPA], 0.84 g, 2.74 mmoles) in 50 ml of dry acetonitrile was allowed to reflux with 0.8 g of 10% palladium-on-carbon under nitrogen for 5 hrs. The catalyst was removed by filtration and was washed repeatedly with acetonitrile. The solvent was removed by distillation in-vacuo to give a dark green oil (0.77 g; yield, 92%), single spot on TLC and was used without further purification in the next step. A solution of the (−)dehydro-MDO-NPA (0.77 g) in absolute ethanol (50 ml) was stirred with 2 g of sodium cyanoborohydride at pH 5 under nitrogen for 24 hrs. Ethanol was distilled off in-vacuo, and the resulting white solid was made basic with 10% sodium carbonate solution and extracted with ethyl acetate. The extract was washed with water, dried over anhydrous MgSO$_4$, filtered and evaporated to dryness. A mixture of (−)dehydro-MDO-NPA and (±)MDO-NPA was separated after silica gel column chromatography using methylene chloride as a solvent. (±)MDO-NPA (0.28 g) was isolated as a yellowish white solid, $[\alpha]_D^{25°} - 1°$ (c, 0.105 in methanol).

The racemate (0.28 g) was resolved by formation of S(+)10,11-methylenedioxy-N-n-propylnoraporphine (−)dibenzoyl-L-tartrate in ethyl acetate, and recrystallized three times from methanol/ethyl acetate (0.255 g); $[\alpha]_D^{25°} - 46.66°$ (c, 0.105 in methanol); m.p. 172°-73°.

A white solid of (+)MDO-NPA-(−)dibenzoyl-L-tartrate was basified with 10% Na$_2$CO$_3$ solution, and extracted with ethyl acetate. The extract was washed with water, dried over anhydrous MgSO$_4$, filtered and evaporated to yield a white solid, which was converted into the hydrochloride salt with ethereal HCl-m.p. 263.65° C. (dec); mass spectrum, m/e 307 (M+); $[\alpha]_D^{25.5°}+41.93°$, $[\alpha]_{546}^{25.5°}+46.23°$ (c 0.093, MeOH).

S(+) 11-Methoxy-N-propylnoraporphine hydrobromide [(+)-11-MePNa]

This compound is prepared by the resolution of (RS)-11-methoxy-N-n-propylnoraporphine, which was prepared by the published procedure of Neumeyer et al.[7] Thus, to a solution of 2 g (0.0068 mol) of (±)11-methoxy-N-n-propylnoraporphine, dissolved in 15 ml ethyl acetate was added a solution of 1.25 g (0.0034 mol) of (+)dibenzoyl-D-tararic acid dissolved in 15 ml ethyl acetate. The mixture was heated to reflux for 30 min and then cooled and filtered. After washing with ethyl acetate, this salt was recrystallized three times from a mixture of 2-propanol and abs. ethanol (1:1) to yield 0.6 g. Further crystallization did not change the specific rotation. The crystalline salt was dissolved in aqueous saturated $K_2CO_3$ solution, and the mixture was extracted with $CH_2Cl_2$. After drying over $MgSO_4$, the extract was converted into the hydrochloride salt to give 320 mg of off-white crystals, of (−)11-OCH$_3$-PNa hydrochloride mp 263°-4°, $[\alpha]_{578}^{25}-73.08°$ (c 0.26, MeOH).

The combined mother liquors containing the R(−) salt were treated with aqueous saturated $K_2CO_3$ solution to liberate the free base, extracted further with $CH_2CL_2$, and the extract dried and evaporated to dryness after filtration. The remaining 0.75 g of oil was dissolved in 10 ml of ethyl acetate and treated with 0.94 g ($2.56\times10^{-3}$ mole) of (−)dibenzoyl-L-tartaric acid, and treated as described above to give 0.77 g of S(+) 11-MeO-PA salt. The crystalline dibenzoyl tartrate salt was converted to the hydrochloride salt to give 450 mg of S(+) 11-OMe-PA-HCl, mp 263°-4° C.; $[\alpha]_{578}^{25}+72.97$ (C 0.23, $CH_3OH$). Anal. calcd. for $C_{20}H_{23}NO\cdot HCl\cdot H_2O$: C, 69.05; H, 7.24. Found: C, 69.13; H, 7.45. Mass spectrum m/e 293 (M+).

S(+) 11-hydroxy-N-propylnoraporphine hydrochloride and hydrobromide

To 200 mg of S(+) 11-MeO-PA hydrochloride dissolved in 5 ml of glacial acetic acid was added 5 ml of hydrobromic acid (48% w/v). The reaction mixture was heated under an atmosphere of $N_2$ at 130° in an oil bath for 4 hr. and then allowed to cool under $N_2$ to yield a white crystalline white solid mp 266°-267° C. dec; $[\alpha]_{578}^{25°}+63.55°$ (c 0.214 MeOH). The pH of the reaction mixture was adjusted to 8 with aq. $Na_2CO_3$ solution, and the liberated free base was extracted from $CH_2Cl_2$ and converted to the hydrochloride salt to yield 120 mg (63%) of S(+)-11-OH-PA HCl, mp 257°-258° C. (dec); $[\alpha]_{578}^{25°}+64.55$ (c 0.11, $CH_3OH$). Anal. calcd. for $C_{19}H_{21}NO\cdot HCl\cdot H_2O$: C, 68.35; H, 6.95, Found: C, 68.32; H, 7.27; Mass spectrum, m/e 279 (M+).

PHARMACOLOGY

Methods

Stereotypy: The mean stereotyped licking and gnawing behavioral rating scheme developed by Tarsy and Baldessarini[8] was used. The maximum score was 3.0. Results shown below in Tables 1 and 2.

Activity: Overall motor activity was measured by use of the self-recording Stoelting electronic activity monitor method described previously by Stewart, Campbell, Sperk, and Baldessarini[9]. Total activity is obtained by setting monitor sensitivity so as to detect both locomotion and small movements (such as grooming, sniffing, and chewing) as would be prominent in stereotyped responses that tend to diminish locomotion and increase sniffing, licking, and chewing movements. Locomotor activity is detected selectively by setting monitor sensitivity to detect large, locomotor movements, and to minimize smaller movements already described. Results are shown in Tables 3-5 and FIG. 2.

Catalepsy: This measure of muscle rigidity is assessed by having animals in abnormal body positions and timing their duration of maintaining these. This is done by placing rats on a wire grid placed at a 45° angle to the benchtop, or by placing their forelimbs on a raised horizontal metal bar, and timing the latency to resume a normal posture by stopwatch. These methods are described in detail by Campbell and Baldessarini[10]. Results are shown in Table 3.

All data presented in the Tables below are expressed as the mean results from 4-6 rats per condition, ±S.E.M. Stereotypy is expressed in rating units (maximum=3.0) and activity is expressed in arbitrary units of percent change, derived from EAM counts per unit time, relative to activity in control (saline) animals set at zero.

Dopamine (DA) sensitive adenylate cyclase activity was evaluated with homogenates of rat corpus striatum[11] and intact pieces of carp retina[12] by similar methods. The ability of aporphines to stimulate the accumulation of 3',5'-cyclic adenosine monophosphate (cAMP) was evaluated in striatal tissue by a protein-binding assay for cAMP (also used for the fish retina cAMP assays) after incubation of the cyclase-rich tissue in the presence of excess ATP and theophylline (rat) or IBMX (fish) to inhibit phosphodiesterase.[11-12] Typical basal activity (DA agonist omitted) (±SEM) with rat striatum was 2.48±0.15 pmol of cAMP formed per 2.5 min assay, and with the fish retinal tissue 0.245±11 pmol/mg protein/5 min. Results are shown in Table 6.

Binding assays were carried out with a membrane fraction (P$_4$) recovered from osmotically shocked and Polytron-disrupted "synaptosomal" preparations of rapidly frozen protease-free calf caudate nuclei. Ligands included (R)-[8,9-$^3$H]apomorphine ([$^3$H]APO: New England Nuclear, 20–30 Ci/mmol), (±)-[5,8-$^3$H]-2-amino-6,7-dihydroxy-1,2,3,4-tetrahydronaphthalene ([$^3$H] ADTN; New England Nuclear, 36 Ci/mmol), and [benzene ring-$^3$H]-spiroperidol ([$^3$H]SPR, New England Nuclear, 30 Ci/mmol). Blanks were defined by adding excess (10 μM) unlabeled (±ADTN in the [$^3$H]APO assays, APO in the [$^3$H]ADTN assay, and (+)-butaclamol (gift of Ayerst Laboratories, New York) with [$^3$H]SPR. Results are shown in Table 7.

Isomeric Substrate Selectivity for COMT. Substrate selectivity for the enantiomers of NPA was tested with partially purified rat liver catechol O-methyl-transferase (COMT). A range of six concentrations of substrate (in triplicate) was tested by incubation with [methyl-$^3$H]S-adenosyl-L-methionine (SAMe; New England Nuclear, 15.3 Ci/mmol). The enzyme was partially purified by ammonium sulfate precipitation and dialysis. The methylated product was recovered selectively in hexane and counted. The methods of purification, assay, and product recovery were essentially those described by Kebabian[13] for methylation of APO to apocodeine. The product obtained with NPA was found to migrate on silica gel TLC and high-voltage paper electrophoresis as a single peak identical in R$_1$ with a sample of authentic (±)-N-n-propylnorapocodeine.[3] In addition, the product that formed from [$^3$H] SAMe with unlabeled NPA and extracted into hexane gave a single radioactive peak in silica gel TLC chromatography with a solvent mixture of toluene/isoamylol (3:2, v/v). The product ($R_f$=0.79) was clearly separated in a single peak from the labeled cofactor (at origin). Kinetic data were evaluated by linear transformation of the data (velocity of product formation$^{-1}$ vs. substrate concentration$^{-1}$) to obtain values for apparent affinity of substrate ($K_c$=negative slope) and maximum reaction velocity ($V_{max}$=y intercept). The results are provided in Table 8.

An experiment shown in Table 9 involves testing the effects of S(+) isomers of apomorphine (APO) and N-propylnorapomorphine (NPA) given systemically (intraperitoneally, ip), as well as S(+) methylenedioxy-N-propylnorapomorphine (MDO-NPA) given ip or orally (po, by orogastric intubation). The testing paradigm was the measurement of behavioral arousal as electonically recorded locomotor activity in the rat given dopamine by local stereotaxic injection into a limbic area of forebrain (nucleus accumbens septi) of dopamine (16 μg dose) following its protection by pretreatment with an inhibitor of monoamine oxidase (nialamide, 100 mg/kg, 2 hours earlier). All conditions involved N=6 rats per dose, and half-maximally inhibitory doses were computed as ID$_{50}$ values (±SEM). Activity was monitored for 30 min after injection of DA into the brain, which was done at 10 min after systemic dosing with an S(+)aporphine test compound.

The results indicate that (+)NPA and (+)MDO-NPA were much more potent inhibitors of DA in the limbic system of the rat than was (+)APO (8 and 13 times more potent, respectively). Also, (+)MDO-NPA was nearly as potent when given orally as by injection (ID$_{50}$=0.5 mg/kg orally and 0.3 mg/kg intraperitoneally).

An experiment shown in Table 10 is similar to that shown in Table 8, except that dopamine (DA) was injected stereotaxically into the central corpus striatum and induced a postural change measured as time spent with head deviated from the midline (out of a total of 12 min of observations over an hour). In this experiment, while DA itself induced head-deviation, there were no antagonistic interactions with DA by any of the S(+)aporphine treatments given by injection or orally. This result supports the impression that the S(+)NPA and S(+)MDO-NPA compounds are not potently active DA antagonists in the basal ganglia, but are regionally selective in the mammalian forebrain to act at limbic sites while sparing the basal ganglia.

An experiment shown in Table 11 involves testing rats for the ability of isomers of 11-substituted N-propylnoraporphines to potentiate or inhibit the locomotor-arousal inducing effects of a moderate dose of R(—)apomorphine (APO), an agonist of forebrain dopamine (DA) receptors, given systemically to intact rats. The results show that the R(—)11-hydroxy compound increased the locomotor stimulatory effect of APO by 51%, and so showed agonistic activity of its own, while the 11-methoxy congener was much less active (increased action of APO by only 14% at the same dose). A more striking effect, however, was a strong inhibitory interaction with APO by the S(+)11-hydroxy-N-propylnoraporphine, (+11-OH-NPa) while the corresponding S(—)11-methoxy congener was devoid of activity.

In an experiment shown in Table 12, the same compounds tested in Table 11 were given to rats with no other treatment, and tested for their ability to induce stereotyped gnawing and other behaviors believed to be mediated by the corpus striatum as a test of activity in this extrapyramidal site in the mammalian forebrain. The R(—)11-hydroxy-N-propylnoraporphine (-11-OH-NPa) showed striking activity as a DA agonist in this test, and its 11-methoxy congener was moderately active. With the S(+)isomers, the 11-methoxy compound was inactive, but the S(+)11-hydroxy-N-propylnoraporphine was also virtually inactive in this test for DA agonist activity.

Taken together, the results of experiments in Tables 11 and 12 indicate that the S(+)11-hydroxy-N-propylnoraporphine analog had strong activity as an antagonist of R(—)APO, the DA agonist with respect to locomotor arousal, believed to represent a stimulation of limbic DA receptors. At the same time, this novel aporphine failed to show activity in the basal ganglia as expressed by inducing sterotyped activity. Thus, it appears that this agent may be a selective limbic DA antagonist, as found previously with the catechol analog, S(+)NPA and its methylenedioxy derivate (see Tables 9 and 10). The results also extend previous impressions that 11-hydroxyl group is critically important for agonistic activity of R(—)aporphines, while S(+) analogs are not active as agonists and 11-methoxy substitution (no free OH group) markedly decreases agonistic activity, presumably by steric hindrance at DA receptors (as paralleled in DA-agonist binding receptor studies in vitro).

Figure 2:
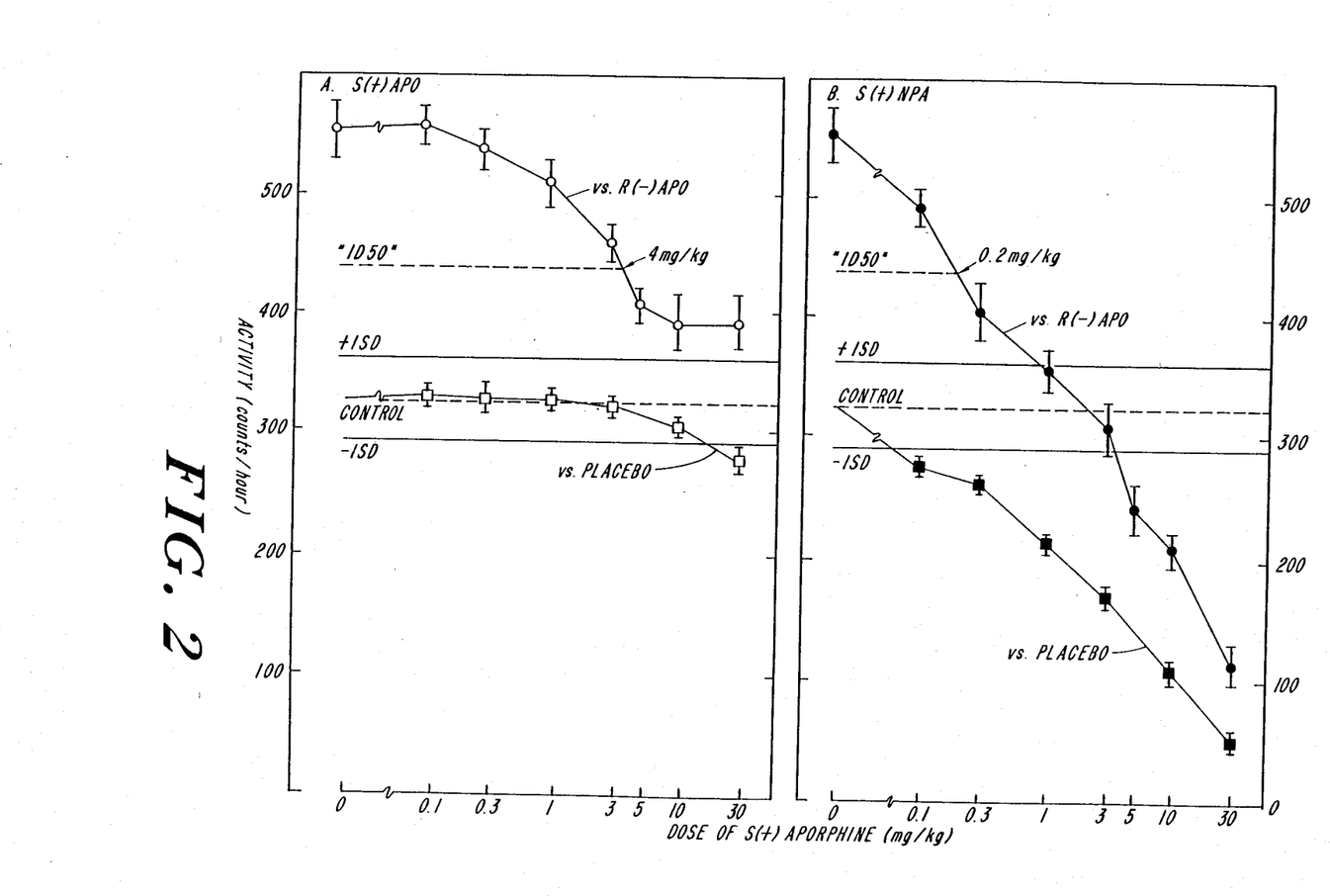

In an experiment depicted in FIG. 2, there was a comparison of effects of (+)APO and (+)NPA on locomotor activity manifested spontaneously or aroused by (—)APO. Rats (mean N=6 per condition) were tested for locomotor activity for 60 min following a single dose of (—)APO (0.3 mg/kg, SC), or its vehicle ("placebo" condition). The S(+) isomers were administered in a range of doses from 0 or 0.1 to 30 mg/kg, SC immediately following injection of (—)APO or its vehicle. Data are presented in FIG. 2 as mean EAM activity counts per hour SEM. In that figure, the dashed line labeled "control" represents the mean activity of rats given vehicle only and no aporphine (SD values are indicated by parallel light lines above and below the control mean). The apparent ID$_{50}$ values are indicated as corresponding to reduction of the maximum effects of (—)APO by half (at dashed lines labeled "ID$_{50}$"), Panel A represents the effects of doses of S(+)APO against (—)APO (0—0) or its vehicle (□—□); Panel B represents the effects of doses of (+)NPA against (—)APO (●—●) or its vehicle (■—■).

RESULTS

Summary Of Preliminary Data

TABLE 1

| Effects of enantiomers of APO and NPA on stereotypy in the rat. | |
|---|---|
| Treatment | Stereotypy Score |
| (—)NPA ± saline | 2.9 ± 0.1 |
| (—)APO ± saline | 3.0 ± 0.0 |
| (+)NPA ± saline | 0.0 ± 0.0 |
| (+)NPA ± (—)NPA | 2.9 ± 0.2 |
| (+)NPA ± (—)APO | 2.9 ± 0.1 |
| (—)NPA ± (+)NPA | 3.0 ± 0.0 |

TABLE 1-continued

Effects of enantiomers of APO and NPA on stereotypy in the rat.

| Treatment | Stereotypy Score |
|---|---|
| (−)APO ± (+)NPA | 2.9 ± 0.1 |

S (+)NPA was given at 5 mg/kg, s.c., at 30 min before, or 30 min after R (−)NPA or R (−)APO were given at 3 mg/kg, s.c. The data indicate that the (−) isomers are strong stereotypy inducers (reflecting DA agonism in basal ganglia), that the (+) isomers are not active alone, or interactive with the (−).

TABLE 2

Lack of Effect of (+)NPA on stereotyped behavior induced by (−)APO.

| Dose of (+)NPA (mg/kg) | Percent of Control |
|---|---|
| 0 | 100.0 ± 6.0 |
| 3 | 100.0 ± 10.6 |
| 5 | 100.0 ± 12.3 |
| 30 | 102.6 ± 8.9 |

Rats were given (−)APO (0.3 mg/kg, or the approximate ED$_{50}$), followed immediately by (+)NPA at the indicated dose, or its vehicle as a control (all IP). Stereotypy scores were rated for one hour as described in Methods, with a maximum possible score of 18.0; the mean control score was 9.23 ± 0.43 (51.3% of maximum). All data are expressed as means ± SEM (N = 6 to 12 rats per condition); no effect of (+)NPA is significant by t-test (p > 0.5).

TABLE 3

Behavioral actions of isomers of NPA.

| Dose (mg/kg, s.c.) | Stereotypy[a] (−)NPA | Stereotypy[a] (+)NPA | Total Activity[b] (−)NPA | Total Activity[b] (+)NPA | Catalepsy[c] (−)NPA | Catalepsy[c] (+)NPA |
|---|---|---|---|---|---|---|
| 0 | 0 | 0 | 0 | 0 | 0 | 0.0 |
| 0.1 | 1.1 ± 0.2 | 0 | 2.0 ± 1.8 | 3.2 ± 1.1 | 0.5 ± 0.2 | 0.6 ± 0.1 |
| 0.3 | 2.0 ± 0.3 | 0 | 2.1 ± 3.2 | −5.2 ± 3.1 | — | 0.4 ± 0.1 |
| 3.0 | 2.9 ± 0.9 | 0 | 231.4 ± 37 | −50.0 ± 18 | 0.8 ± 0.3 | 0.6 ± 0.1 |
| 5.0 | 3.0 ± 0.0 | 0 | — | −52.1 ± 21 | — | 0.6 ± 0.1 |

The data indicated that (−)NPA has strong stereotypy-inducing, and total activity increasing actions (reflecting DA agonistic actions in the basal ganglia and limbic areas, respectively). (+)NPA lacks these actions, but inhibits spontaneous motor activity. Neither enantiomer induces appreciable catalepsy. Note that the minus values indicate a percentage lowering of activity below the level in saline controls (0).
[a]Stereotypy Score: maximum response = 3.0
[b]Activity: expressed as percent change vs. placebo-control
[c]Catalepsy score: maximum = 18.0

TABLE 4

Interactions of S(+)APO with behavioral effects of R(−)APO.

| Pretreatment Dose of (−)APO, mg/kg | A Stereotypy Score Saline | A Stereotypy Score (+)APO | B Total Activity Saline | B Total Activity (+)APO | C Locomotion Saline | C Locomotion (+)APO |
|---|---|---|---|---|---|---|
| 0 | 0.12 ± 0.06 | 0.32 ± 0.62 | 0 | −0.62 ± 0.33 | 0 | −0.84 ± 0.22 |
| 0.3 | 1.62 ± 0.23 | 0.89 ± 0.36 | 42.2 ± 8.5 | 36.2 ± 0.92 | 63.5 ± 12.3 | 36.2 ± 4.3 |
| 1.0 | 2.09 ± 0.36 | 1.92 ± 0.21 | 51.9 ± 6.8 | 44.6 ± 0.75 | 75.8 ± 19.4 | 43.0 ± 5.2 |
| 3.0 | 2.92 ± 0.20 | 2.93 ± 0.32 | 75.3 ± 8.6 | 62.0 ± 0.48 | 48.6 ± 9.3 | 42.1 ± 6.3 |

All the post-treatment doses of (+)APO were 3.0 mg/kg, s.c. The data indicate that (−)APO alone stimulates activity and stereotypy, but that (+)APO has little inhibitory action vs. (−)APO-induced stereotypy, but a large interaction to inhibit the locomotor component of general arousal and activity, selectively, especially after lower doses of (−)APO, selective for limbic, arousal-inducing areas.

TABLE 5

Interactions of S(+)NPA with R(−)NPA.

| Pretreatment Dose of (−)NPA, mg/kg | A Stereotypy Score Saline | A Stereotypy Score (+)NPA | B Total Activity Saline | B Total Activity (+)NPA | C Locomotion Saline | C Locomotion (+)NPA |
|---|---|---|---|---|---|---|
| 0 | 0 | 0 | 0 | 0 | 0 | 0 |
| 0.3 | 2.0 ± 0.2 | 1.7 ± 0.6 | 22.1 ± 3.7 | 18.8 ± 2.6 | 48.1 ± 9.2 | 14.8 ± 2.6 |
| 3.0 | 2.8 ± 0.4 | 2.9 ± 0.8 | 231.4 ± 37 | 156.7 ± 26 | 10.2 ± 6.3 | 8.5 ± 0.6 |

All post-treatment doses of (+)NPA were 3 mg/kg, s.c. The data are similar to those in Table 3, indicating that (+)NPA does not interact appreciably vs. (−)NPA-induced stereotypy, but does seem to inhibit the locomotor component of arousal induced by (−)NPA, especially at low doses of the latter with less stereotypy activity.

TABLE 6

Stimulation of Formation of Cyclic AMP in Rat Striatal Homogenate.

| addition | concn. μM | cAMP production (N) | % of control |
|---|---|---|---|
| blank | 0 | 2.48 ± 0.15 (12) | 100 |
| DA | 50 | 5.39 ± 0.19 (12) | 217 |
| (−)-NPA | 1 | 3.71 ± 0.31 (6) | 150 |
|  | 5 | 4.57 ± 0.13 (10) | 184 |
|  | 10 | 5.34 ± 0.27 (12) | 215 |
|  | 50 | 5.71 ± 0.24 (12) | 230 |
|  | 100 | 5.56 ± 0.24 (5) | 224 |
| (+)-NPA | 10 | 2.95 ± 0.19 (12) | 119 |
|  | 100 | 3.19 ± 0.16 (6) | 129 |

Stimulation of the formation of cyclic AMP (cAMP) with isomers of NPA was assayed in homogenates of corpus striatum obtained from rat brain. The method of assay of the activity of DA-sensitive adenylate cyclase by the rate of formation of cAMP above a basal (no agonist) level is described under Experimental Section. The data are mean values of cAMP levels in picomoles per 2.5 min of assay plus or minus SEM. The concentration that increased cAMP by 50% (EC$_{30}$) is ca. 1 μM for (R)-(−)-NPA and much higher than 100 μM for (S)-(+)-NPA [potency ratio > 100 in favor of the (R)-(−) isomer].

TABLE 7

Affinity of Isomers of N—n-Propylnorapomorphine (NPA) for Dopamine Receptors.

| ligand (nM) | IC$_{50}$, ηM (R)-(−)-NPA | IC$_{50}$, ηM (±)-NPA | IC$_{50}$, ηM (S)-(+)-NPA |
|---|---|---|---|
| [³H] APO (0.5) | 2.5 | 5.0 | 66 |
| [³H] ADTN (0.5) | 2.0 | 3.5 | 60 |

TABLE 7-continued

Affinity of Isomers of N—n-Propylnorapomorphine (NPA) for Dopamine Receptors.

| ligand (nM) | IC$_{50}$, ηM | | |
|---|---|---|---|
| | (R)-(−)-NPA | (±)-NPA | (S)-(+)-NPA |
| [$^3$H] SPR (0.15) | 174 | 670 | 1414 |

Fractions (P$_4$) of caudate nucleus from calf brain were prepared and incubated with low concentrations of tritiated apomorphine (APO), ADTN, or spiroperidol (SPR) as ligands in competition with a range of concentrations of the NPA isomers indicated, as described under Experimental Section. Values of IC$_{34}$ were computed from log probit analyses of data from at least three determinations involving at least four concentrations of each aporphine. The tabulated values are means, the SD of which were 5% or less.

TABLE 8

Isometric Preference of Rat Liver COMT for NPA as Substrate.

| agent | K$_m$, μM | V$_{max}$ (pmol/assay)/h |
|---|---|---|
| (+)-NPA | 0.48 | 11.7 |
| (−)-NPA | 0.94 | 10.0 |

Data are mean values obtained by kinetic analyses of double-reciprocal plots of (reaction velocity)$^{-1}$ vs. (substrate concentration)$^1$ with (−)-NPA and (+)-NPA as substrates, to allow computation of values for apparent K$_d$ (negative slope) and apparent V$_{max}$ (Y intercept). Two separate experiments were carried out as described under Experimental Section with six substrate concentrations assayed in triplicate. The ranges of values for V$_{max}$ were 8.9–11.1 vs. 10.2–13.2 and for K$_d$ were 0.93–0.95 vs. 0.41–0.55 for (R)(−)- vs. (S)(+)-NPA, respectively. These results indicate a somewhat higher apparent affinity for the (S)-(+)-isomer (in contrast to results pertinent to DA receptors) but little difference in velocity of methylation at saturating substrate concentrations.

TABLE 9

Effects of aporphines on arousal induced by 16 μg DA in rat accumbens.

| Dose (mg/kg) | (+)APO (ip) | (+)NPA (ip) | (+)MDO-NPA (ip) | (+)MDO-NPA (po) |
|---|---|---|---|---|
| 0 (control) | 238 ± 38 | 238 ± 38 | 238 ± 38 | 238 ± 38 |
| 0.3 | 246 ± 41 | 139 ± 17 | 122 ± 16 | 149 ± 23 |
| 1.0 | 190 ± 37 | 80 ± 11 | 54 ± 9 | 74 ± 17 |
| 3.0 | 125 ± 19 | 54 ± 10 | 36 ± 7 | 49 ± 16 |
| ID$_{50}$ | 3.6 | 0.45 | 0.27 | 0.51 |

Data are mean activity counts ± SEM (N = 6) for rats given DA into the medial accumbens after pretreatment with an inhibitor of monoamine oxidase (MA0), and monitored on EAM for 30 min (aporphine given 10 min before DA systemically-intraperitoneally [ip] or orally [po]).

TABLE 10

Effects of aporphines on head posture in rat after intrastriatal DA

| Treatment (Route) | | Contralateral Head Deviation | |
|---|---|---|---|
| Intrastriatal | Systemic | Time (sec) | Percent of Total |
| Saline | Saline | 238 ± 41 | 33.1 |
| Dopamine | Saline | 425 ± 53 | 59.0 |
| Dopamine | (+)APO | 412 ± 53 | 57.2 |
| Dopamine | (+)NPA | 480 ± 44 | 66.7 |
| Dopamine | (+)MDO-NPA (ip) | 512 ± 96 | 71.7 |
| Dopamine | (+)MDO-NPA (po) | 505 ± 89 | 70.1 |

Rats given 16 μg DA into striatum after an MAO inhibitor; head posture timed for 12 min (1 min each 5 min × 1 hr) after DA given 10 min after an aporphine. Data are means ± SEM (N = 6). Only the effect of DA itself is significant; no aporphine inhibited DA (all given at 3 mg/kg).

TABLE 11

Interactions between (−)apomorphine and novel N—propylaporphines as indicated by locomotor activity in the rat.

| Test Agent | EAM Score ± SEM | Percent of Control |
|---|---|---|
| (−)APO alone (control) | 505 ± 55 | 100 |
| (+)11-OH—N—propylnoraporphine | 218 ± 33 | 43* |
| (+)11-methoxy-N—propylnoraporphine | 528 ± 25 | 105 |
| (−)11-OH—N—propylnoraporphine | 764 ± 58 | 151 |
| (−)11-methoxy-N—propylnoraporphine | 574 ± 45 | 114 |

Test agents (11-substituted-N—propylnoraporphine isomers were given at a dose of 3 mg/kg, ip (in 2 ml/kg) just prior to (−)apomorphine (APO, at 0.3 mg/kg, ip, in 1 ml/kg) to rats (N = 6) tested in an electronic activity monitor for 60 min. The results show a significant inhibition of arousal by S(+)11-hydroxy-N—propylnoraporphine only (*p < 0.005 by t-test) and a trend toward agonistic activity of the R(−) isomer of this monohydroxy compound, while the methoxy analogs lacked activity as agonists or antagonists.

TABLE 12

Stereotyped activity induced by novel N—propylaporphines in the rat

| Test Agent | SB Score ± SEM | Percent of Maximum |
|---|---|---|
| (−)11-OH—N—propylnoraporphine | 13.8 ± 0.75 | 76.7 |
| (−)11-methoxy-N—propylnoraporphine | 6.5 ± 0.50 | 36.1 |
| (+)11-OH—N—propylnoraporphine | 1.3 ± 0.75 | 6.9 |
| (+)11-methoxy-N—propylnoraporphine | 0 ± 0 | 0.0 |

Rats (N = 4 per condition) were given 3 mg/kg, ip (in 2 ml/kg) of each test aporphine and rated for stereotyped behaviors (SB) each 10 min for one hour thereafter (max. possible score = 18.0). The results indicate that the R(−)-11-hydroxy-N—propylnoraporphine is very active as an apparent DA agonist in forebrain, while the respective S(+) isomers were virtually or totally inactive. The R(−)11-methoxy analog had some activity, but was weaker than the congener with a free 11-hydroxyl group.

TABLE 13

Effect of metabolic inhibitor SKF-525A on behavioral effect of (+)MDO-NPA

| Pretreatment | Treatment | Locomotor Activity ± SEM (counts/hr) | (%) |
|---|---|---|---|
| Saline | Saline | 4210 ± 317 | (100) |
| Saline | S(+)MDO-NPA | 1828 ± 265 | (43)* |
| SKF-525A | Saline | 4777 ± 610 | (113) |
| SKF-525A | S(+)MDO-NPA | 3445 ± 597 | (82) |

Rats (N = 6) per condition were tested by monitoring locomotor activity on an electronic monitor under high-arousal conditions (7–8 PM during early "lights out" phase, and singly in previously occupied test cages). Pretreatment was saline (control) or the microsomal inhibitor SKF-525A (40 mg/kg, ip). At 30 min later, saline or (+)MDO-NPA (3 mg/kg, ip) was given, and the rats were monitored for the next 60 min. Data are activity counts per hour, as means ± SEM ([*] = significant by t-test at p < 0.05). The results indicate that the metabolic inhibitor marked counteracted the behavioral depresssion induced by the aporphine, while having little excitatory action of its own. This result is consistent with the hypothesis that the methylenedioxy aporphine acts as a "prodrug" to free S(+) NPA.

REFERENCES

1. Matthiesson, A.; Wright, C. P. A.; Proc. R. Soc. Ser B, London 1869, 17, 455.
2. Koch, M. V.; Cannon, J. G.; Burkman, A.; J. Med. Chem. 1968, 11, 977.
3. Neumeyer, J. L.; Neustadt, B. R.; Oh, K. H.; Weinhardt, K. K.; Boyce, C. B.; Rosenberg, F. J.; Teiger, D. G.; J. Med. Chem. 1973, 16, 1223.
4. Cava, M. P.; Edie, D. L.; See J. J.; J. Org. Chem. 1975, 40, 301.
5. Davis, P. J.; Seyhan, S.; Soine, W.; Smith, R. V.; J. Pharm. Sci. 1980, 69, 1056.
6. Campbell, A.; Baldessarini, R. J.; Ram, V. J.; and Neumeyer, J. L.; Neuropharmacology 1982, 21, 953.
7. Neumeyer, J. L.; Granchelli, F. E.; Fuxa, K.; Ungerstedt, V.; and Corrodi, H.; J. Med. Chem. 1974, 17, 1090.
8. Tarsy, D.; Baldessarini, R. J.; Neuropharmacology 1974, 13, 927.

9. Stewart, R. M.; Campbell, A.; Sperk, G.; Baldessarini, R. J.; Psychopharmacology 1979, 60, 281.
10. Campbell, A.; Baldessarini, R. J.; Psychopharmacology 1981, 73, 219.
11. Baldessarini, R. J.; Walton, K. G.; Kuls, N. S.; Eur. J. Pharmacol. 1979, 56, 167.
12. Watling, K. J.; Williams, M.; Eur. J. Pharmacol. 1982, 77, 321.
13. Kebabian, J. W.; J. Neurochem. 1978, 30, 1143.

What is claimed is:

1. The (S) enantiomers of compounds having the following structure:

wherein $R_1$ is lower alkyl of 2 to 6 carbon atoms, cycloalkyl of 3 to 8 carbon atoms, lower alkenyl, lower alkynyl, phenyl lower alkylene, phenyl lower alkenyl and phenyl lower alkynyl and pharmaceutically acceptable acid addition salts thereof.

2. An orally effective compound being the (S) enantiomer of the structure wherein $R_1$ is lower alkyl, of 2 to 6 carbon atoms, cycloalkyl of 3 to 8 carbon atoms, lower alkenyl, lower alkynyl, phenyl lower alkylene, phenyl lower alkenyl, and phenyl lower alkynyl and $R_2$ and $R_3$ are hydrogen, methyl, or $R_1$, and pharmaceutically acceptable acid addition salts thereof.

3. (S)-(+)N-n-propylnorapomorphine.
4. (S)-(+)-dimethoxy-N-n-propylnorapormorphine.
5. (S)-(+)-methylenedioxy-N-n-propylnoraporphine.
6. The compound of claim 2 wherein $R_2$ and $R_3$ are hydrogen.
7. The (S) enantiomers of compounds having the following structure:

wherein $R_1$ is lower alkyl, of 2 to 6 carbon atoms, cycloalkyl of 3 to 8 carbon atoms, lower alkenyl, lower alkynyl, phenyl lower alkylene, phenyl lower alkenyl and phenyl lower alkynyl and pharmaceutically acceptable acid addition salts thereof and $R_4$ is hydrogen, methyl, lower alkyl or $R^1CO$ where $R^1$ = methyl or lower alkyl.

8. S(+)11-hydroxy-N-propylnoraporphine.
9. S(+)11-Methoxy-N-propylnoraporphine.
10. A method for selectively exerting antipsychotic or sedative effects in the limbic region comprising administering a therapeutically effective amount of a pharmaceutical composition of the compound of claims 1, 2, 3, 4, 5, 6, 7, 8 or 9.
11. A method for selectively exerting antipsychotic effects in the limbic region comprising orally adminstering a therapeutically effective amount of a pharmaceutical composition of a compound of claims 2, 5, 7, or 8.
12. A method for selectively exerting antipsychotic or sedative effects in the limbic region comprising orally administering a therapeutically effective amount of a pharmaceutical composition of the compound of claim 6.

* * * * *

UNITED STATES PATENT AND TRADEMARK OFFICE
CERTIFICATE OF CORRECTION

PATENT NO. : 4,687,773
DATED : August 18, 1987
INVENTOR(S) : John L. Neumeyer; Ross J. Baldessarini It is certified that error appears in the above-identified patent and that said Letters Patent is hereby corrected as shown below:

<u>In the Abstract</u> - Page 2, Column 2

2nd line, before "alkyl substituted cycloalkyl," insert
              --cycloalkyl,--

7th line, after "methyl, or $R_1$" insert $R_1$ is as above
$R_4$ is H, $CH_3$, lower alkyl, or $R^1CO$ -
where $R^1 = CH_3$ or lower alkyl

UNITED STATES PATENT AND TRADEMARK OFFICE
CERTIFICATE OF CORRECTION

PATENT NO. : 4,687,773

DATED : August 18, 1987

INVENTOR(S) : John L. Neumeyer; Ross J. Baldessarini

It is certified that error appears in the above-identified patent and that said Letters Patent is hereby corrected as shown below:

Column 5, line 9, "dehydoraprophine" should read --dehydroaporphine--

Column 7, line 13, "(+)dibenzoyl-D-tararic" should read --(+)dibenzoyl-D-tartaric--

Column 9, line 20, "electonically" should read --electronically-- line 67, "S(-)11-methoxy congener" should read --S(+)11-methoxy congener--

Column 10, line 25, "derivate" should read --derivative--

In Table 3 (paragraph after table)

Column 11, @34, "DA agonostic" should read --DA agonistic--
Column 11, @35, "Neither enantioner" should read --Neither enantiomer--

In Table 7 (3rd line of heading)

Column 12, @55, "$IC_{50}$, η M" should read --$IC_{50}$, μM--
Column 13, @ 5, "$IC_{50}$, η M" should read --$IC_{50}$, μM--

In Table 13 (paragraph after table)

Column 14, @41, "(N=6) per condition)" should read
@46, --(N=6 per condition)
Column 14, @46, "depresssion" should read --depression--

UNITED STATES PATENT AND TRADEMARK OFFICE
CERTIFICATE OF CORRECTION

PATENT NO. : 4,687,773

DATED : August 18, 1987

INVENTOR(S) : John L. Neumeyer; Ross J. Baldessarini

It is certified that error appears in the above-identified patent and that said Letters Patent is hereby corrected as shown below:

Column 16, line 5, "4. (S)-(+)-dimethoxy-N-n-propylnorapor-morphine" should read --4. (S)-(+)-dimethoxy-N-n-propylnorapomorphine--

Signed and Sealed this

Ninth Day of May, 1989

Attest:

DONALD J. QUIGG

Attesting Officer

Commissioner of Patents and Trademarks